(12) United States Patent
Fergason

(10) Patent No.: US 9,867,737 B2
(45) Date of Patent: Jan. 16, 2018

(54) AUTO-DARKENING FILTER OF WELDING SHIELD

(71) Applicants: John David Fergason, Los Altos, CA (US); Anthony Wang Lee, Tainan (TW)

(72) Inventor: John David Fergason, Los Altos, CA (US)

(73) Assignees: John David Fergason, Los Altos, CA (US); Anthony Wang Lee, Tainan (TW)

( * ) Notice: Subject to any disclaimer, the term of this patent is extended or adjusted under 35 U.S.C. 154(b) by 0 days.

(21) Appl. No.: 14/725,559

(22) Filed: May 29, 2015

(65) Prior Publication Data

US 2016/0346131 A1 Dec. 1, 2016

(51) Int. Cl.
*G01J 1/44* (2006.01)
*A61F 9/06* (2006.01)
*G01J 1/18* (2006.01)
*G01J 1/26* (2006.01)
*G02F 1/133* (2006.01)
*G01J 1/02* (2006.01)

(52) U.S. Cl.
CPC ............... *A61F 9/065* (2013.01); *G01J 1/18* (2013.01); *G01J 1/26* (2013.01); *G01J 2001/0276* (2013.01); *G02F 1/13318* (2013.01)

(58) Field of Classification Search
CPC .......... A61F 9/065; G06M 7/00; B23K 26/04; G01J 1/44; G02F 1/13318; G02F 1/137
USPC ...... 250/221, 238, 239, 203.2, 214 A; 2/8.2, 2/8.3, 8.7, 8.8; 362/293
See application file for complete search history.

(56) References Cited

U.S. PATENT DOCUMENTS

2005/0001155 A1* 1/2005 Fergason ................. B23K 9/32
250/221

\* cited by examiner

*Primary Examiner* — Georgia Y Epps
*Assistant Examiner* — Don Williams
(74) *Attorney, Agent, or Firm* — Rabin & Berdo, P.C.

(57) ABSTRACT

An auto-darkening filter of a welding shield has a brightness-sensing unit, an optical shutter and a processor. The brightness-sensing unit generates a first signal or a second signal. In a high-sensitivity mode, the processor controls the optical shutter to operate in a dark state or a bright state depending on intensity of the first signal being higher or lower than a threshold value. In a low-sensitivity mode, the processor controls the optical shutter to operate in the bright state when intensity of the second signal is lower than the threshold value, and automatically change to the high-sensitivity mode from the low-sensitivity mode when intensity of the second signal is higher than the threshold value.

4 Claims, 4 Drawing Sheets

AUTO-DARKENING FILTER OF WELDING SHIELD

BACKGROUND OF THE INVENTION

1. Field of the Invention

The present invention relates to an auto-darkening filter, and more particularly to an auto-darkening filter of a welding shield.

2. Description of Related Art

A welding helmet is a type of headgear. A user who performs welding fabrication process to a work piece should wear the welding helmet to protect the face, eyes and neck from flash burn, ultraviolet light, sparks, heat and toxic welding gas.

Auto-darkening filter is an electro-optical device equipped on the welding helmet. The auto-darkening filter operates in a bright state until an optical sensor thereon detects welding arc. In the bright state, the auto-darkening filter allows the user to retain full vision to see the work piece and surroundings. When the optical sensor detects a light source (such as welding arc) with brightness higher than a threshold, the auto-darkening filter is switched to a dark state to shade the user's eyes from the welding arc.

After the welding fabrication process is accomplished, the user may use a grinding machine to grind the work piece. Sparks are often produced from contact position between the grinding machine and the work piece. However, during the grinding process, whole brightness including the sparks and surroundings sensed by the auto-darkening filter would sometimes be higher than the threshold. This can make it difficult to complete the grinding process properly because the user would lose vision when the auto-darkening filter is being darkened.

SUMMARY OF THE INVENTION

An objective of the present invention is to provide an auto-darkening filter of a welding shield comprising a brightness-sensing unit, an optical shutter and a processor.

The brightness-sensing unit generates a first signal or a second signal. The first signal is obtained from a base signal scaled by M time(s). The second signal is obtained from the base signal scaled by N time(s), wherein N<M.

The optical shutter operates in a bright state or a dark state.

The processor is connected between the brightness-sensing unit and the optical shutter. When the processor operates in a higher-scaled-signal mode, the processor controls the brightness-sensing unit to generate the first signal, controls the optical shutter to operate in the dark state during a period that the first signal is higher than a threshold value, and controls the optical shutter to operate in the bright state during a period that the first signal is lower than the threshold value.

The processor changes to a lower-scaled-signal mode from the higher-scaled-signal mode when a change-mode command is received. In the lower-scaled-signal mode, the processor controls the brightness-sensing unit to generate the second signal, controls the optical shutter to operate in the bright state during a period that the second signal is lower than the threshold value, and changes to the higher-scaled-signal mode from the lower-scaled-signal mode when the second signal is higher than the threshold value.

The auto-darkening filter of the present invention is switchable between the higher-scaled-signal mode and the lower-scaled-signal mode. The higher-scaled-signal mode is applied for welding fabrication process for protecting the user's eye from welding arc. The lower-scaled-signal mode is applied for grinding process for allowing the user to retain full vision of the user's grinding work and surroundings.

Because magnification N in the lower-scaled-signal mode is lower than magnification M in the higher-scaled-signal mode, during grinding process, the second signal corresponding to brightness of sparks and surroundings is hardly higher than the threshold value. As a result, the optical shutter is kept in the bright state during the grinding process, such that the user would not lose vision needed for completing the grinding process properly.

Besides, when the user performs the welding fabrication process again and a new welding arc is struck, the processor in the lower-scaled-signal mode can determine that the second signal corresponding to brightness of the welding arc is higher than the threshold value, and then automatically return to the higher-scaled-signal mode to protect the user's eyes from welding arc. The user needs not manually switch the auto-darkening filter to operate in the higher-scaled-signal mode from the lower-scaled-signal mode. Hence, convenience in use is another advantage of the present invention.

DETAILED DESCRIPTION OF THE PREFERRED EMBODIMENT

An auto-darkening filter (ADF) is an electro-optical device adapted to be mounted on a welding shield, such as a welding helmet or a welding mask. A user who performs welding fabrication process to a work piece is required to wear the welding helmet or position the welding mask in front of the user's face to protect the user's face, eyes and neck from flash burn, ultraviolet light, sparks, heat and toxic welding gas.

Figure 1:
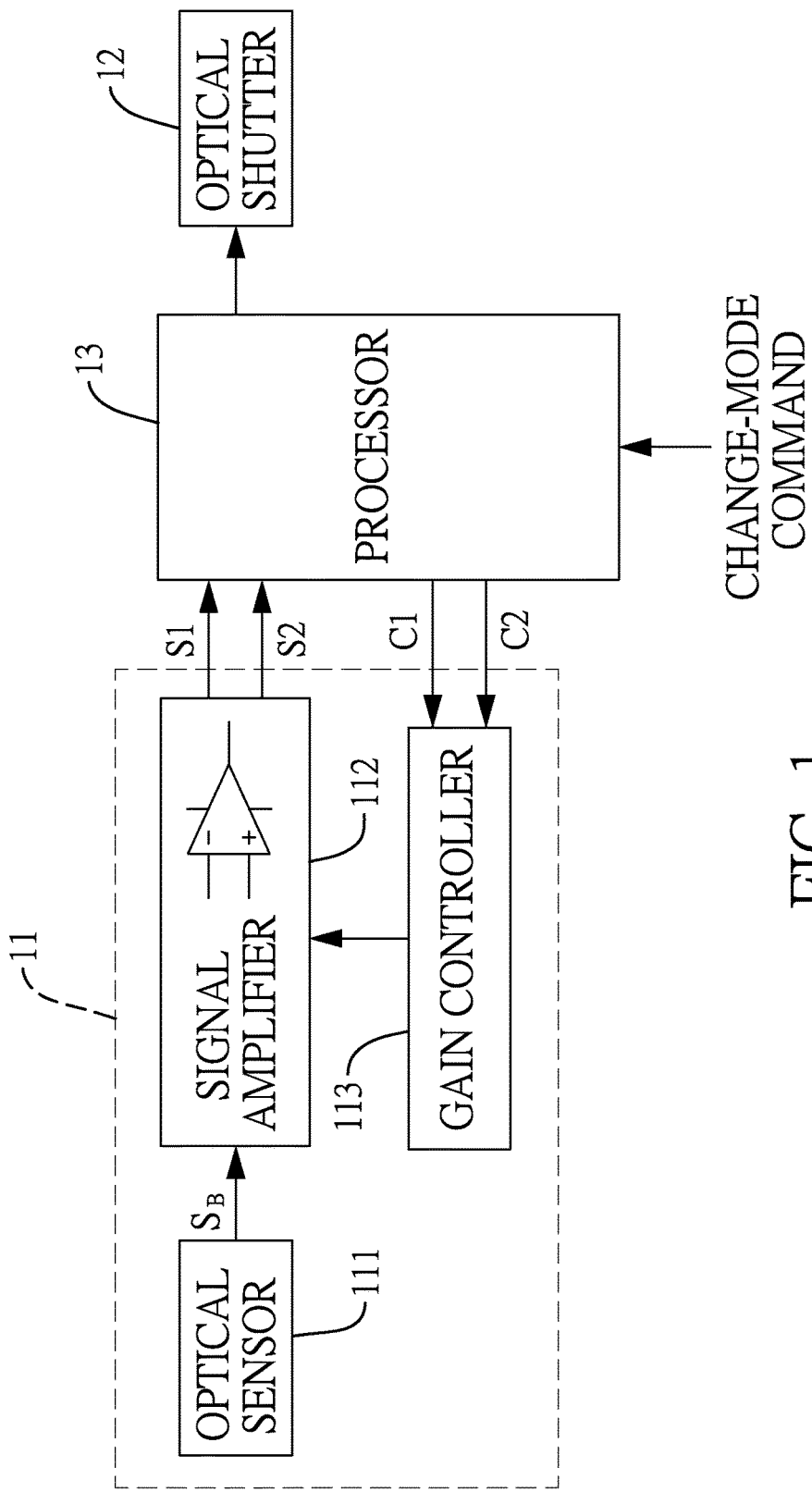
FIG. 1 is a circuit block diagram of an auto-darkening filter of the present invention.

With reference to FIG. 1, the auto-darkening filter of the present invention comprises a brightness-sensing unit 11, an optical shutter 12 and a processor 13. The brightness-sensing unit 11 comprises an optical sensor 111, a signal amplifier 112 and a gain controller 113.

Figure 2:
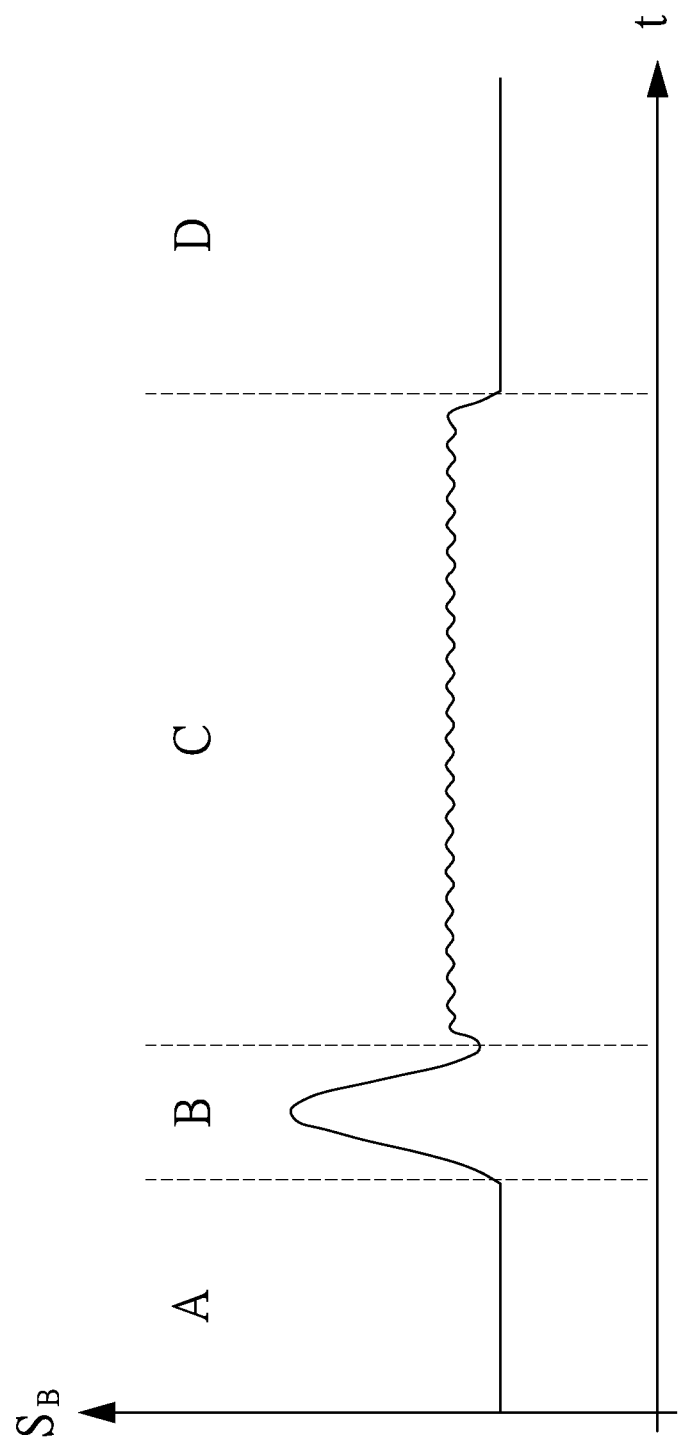
FIG. 2 is a waveform diagram of a base signal.

The optical sensor 111 senses environmental brightness and accordingly generates a base signal $S_B$. Intensity of the base signal $S_B$ is directly proportional to the environmental brightness sensed by the optical sensor 111. With reference to FIG. 2, a waveform diagram shows that the base signal $S_B$ during welding fabrication process is time-varying, and is similar to an AC (alternating current) signal. In time period A, the base signal $S_B$ approximates constant, which means the welding fabrication process has not started yet. In time period B, the base signal $S_B$ has a peak value, which means the welding fabrication process is just started, such that time period B corresponds to ignition of welding arc. Afterwards, the base signal $S_B$ in time period C corresponds to sustained welding arc, so the brightness in time period C is still higher than the brightness in time period A. When the welding fabrication process is finished and the welding arc disappears, the intensity of the base signal $S_B$ in time period D is decreased.

The signal amplifier 112 has an input terminal, a control terminal and an output terminal. The input terminal is electrically connected to the optical sensor 111 to receive the base signal $S_B$. The control terminal is electrically connected to an output terminal of the gain controller 113.

The processor 13 has a first input terminal, a second input terminal, a first output terminal and a second output terminal. The first input terminal is electrically connected to the output terminal of the signal amplifier 112. The second input terminal can be electrically connected to a button or a switch disposed on the welding shield. The first output terminal is electrically connected to an input terminal of the gain controller 113. The second output terminal is electrically connected to the optical shutter 12.

The optical shutter 12 can be a liquid crystal shutter and is switchable between a dark state and a bright state. The optical shutter 12 has better lightproof capability when operating in the dark state than operating in the bright state. For example, in the bright state, the optical shutter 12 is clear and allows the user to retain full vision of the user's work piece and surroundings. In the dark state, the optical shutter 12 is darkened to shade the user's eyes from welding arc.

Figure 3:
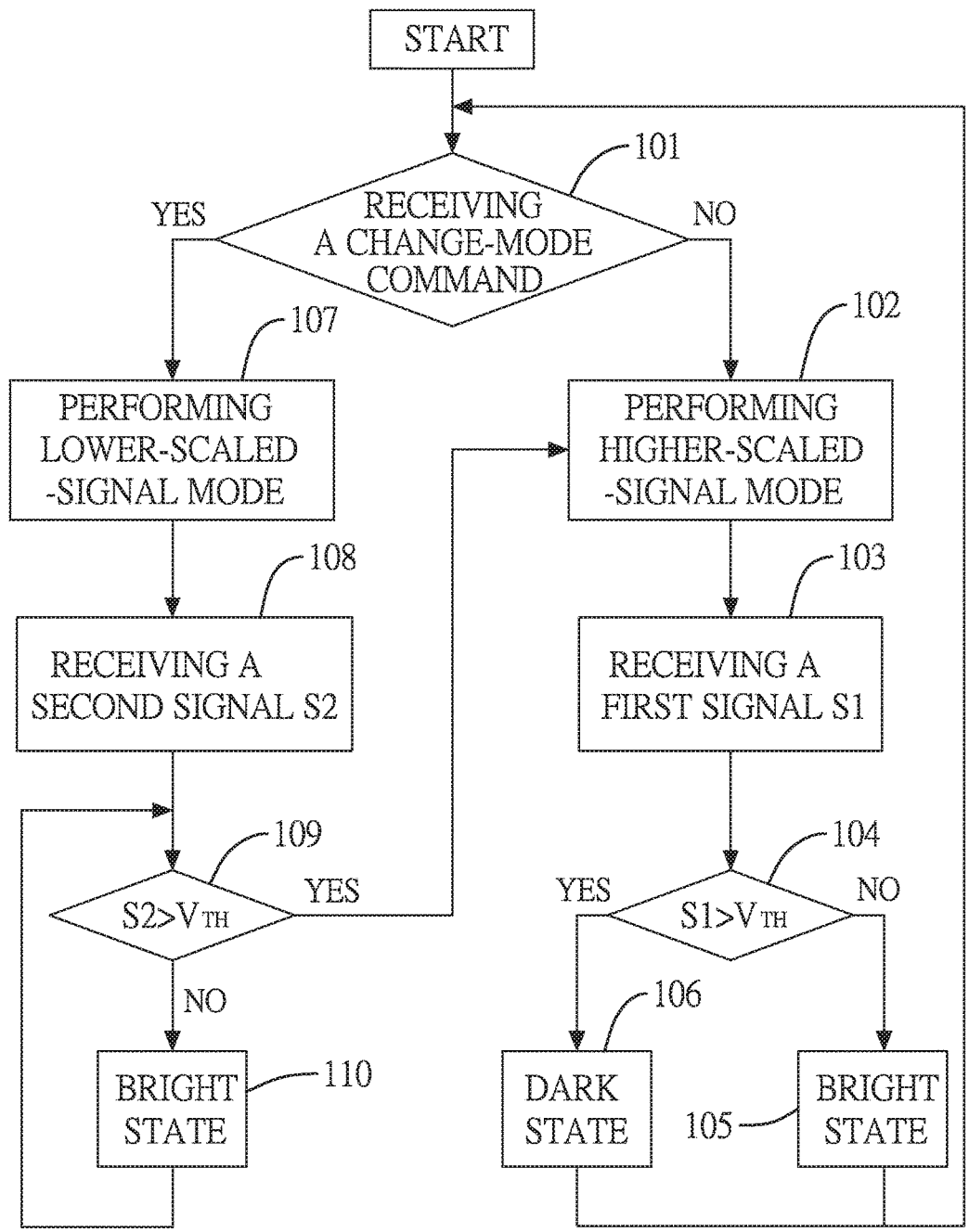
FIG. 3 is a flow chart performed by the auto-darkening filter of the present invention.

With reference to FIG. 3, a flow chart showing operations of the processor 13 of the auto-darkening filter is illustrated. At first, the processor 13 determines whether a change-mode command is received (STEP 101). In this embodiment, when the button or the switch is pressed by the user, the processor 13 correspondingly receives the change-mode command. Otherwise, when the button or the switch is not pressed, the processor 13 does not receive the change-mode command.

When the processor 13 does not receive the change-mode command, the processor 13 performs a higher-scaled-signal mode (STEP 102). With reference to FIG. 1, in the higher-scaled-signal mode, the processor 13 controls the brightness-sensing unit 11 to generate a first signal S1, such that the processor 13 can receive the first signal S1 from the brightness-sensing unit 11 (STEP 103). In this embodiment, the processor 13 sends a first control command C1 to the gain controller 113. According to the first control command C1, the gain controller 113 activates the signal amplifier 112 to scale the intensity of the base signal $S_B$ by M time(s) to produce the first signal S1, wherein M is a positive number. For example, with reference to FIG. 4, when M is larger than 1, the base signal $S_B$ is scaled up by M times to form the first signal S1. The first signal S1 is M times larger than the base signal $S_B$.

When the processor 13 receives the first signal S1, the processor 13 determines whether the intensity of the first signal S1 is higher than a threshold value $V_{TH}$ (STEP 104). When the intensity of the first signal S1 is lower than the threshold value $V_{TH}$, the processor 13 controls the optical shutter 12 to operate in the bright state, such that the user can see the surroundings via the optical shutter (STEP 105). Inversely, when the intensity of the first signal S1 is higher than the threshold value $V_{TH}$, which means the welding arc occurs, the processor 13 controls the optical shutter 12 to operate in the dark state (STEP 106). Hence, during the welding fabrication process, the optical shutter 12 can be automatically switched to the dark state to shade the user's eyes from welding arc.

After the welding fabrication process is finished, the user may use a grinding machine to grind the work piece. In the grinding process, sparks are often produced from contact position between the grinding machine and the work piece. Although the brightness of sparks is much lower than that of welding arc, the whole brightness including the sparks and surroundings during the grinding process is still possible to be higher than the threshold value $V_{TH}$. In order to prevent the optical shutter 12 from being switched to the dark state during the grinding process to affect the user's vision, the user can press the button on the welding shield. Afterward, the processor 13 receives the change-mode command to change to a lower-scaled-signal mode from the higher-scaled-signal mode (STEP 107).

Figure 4:
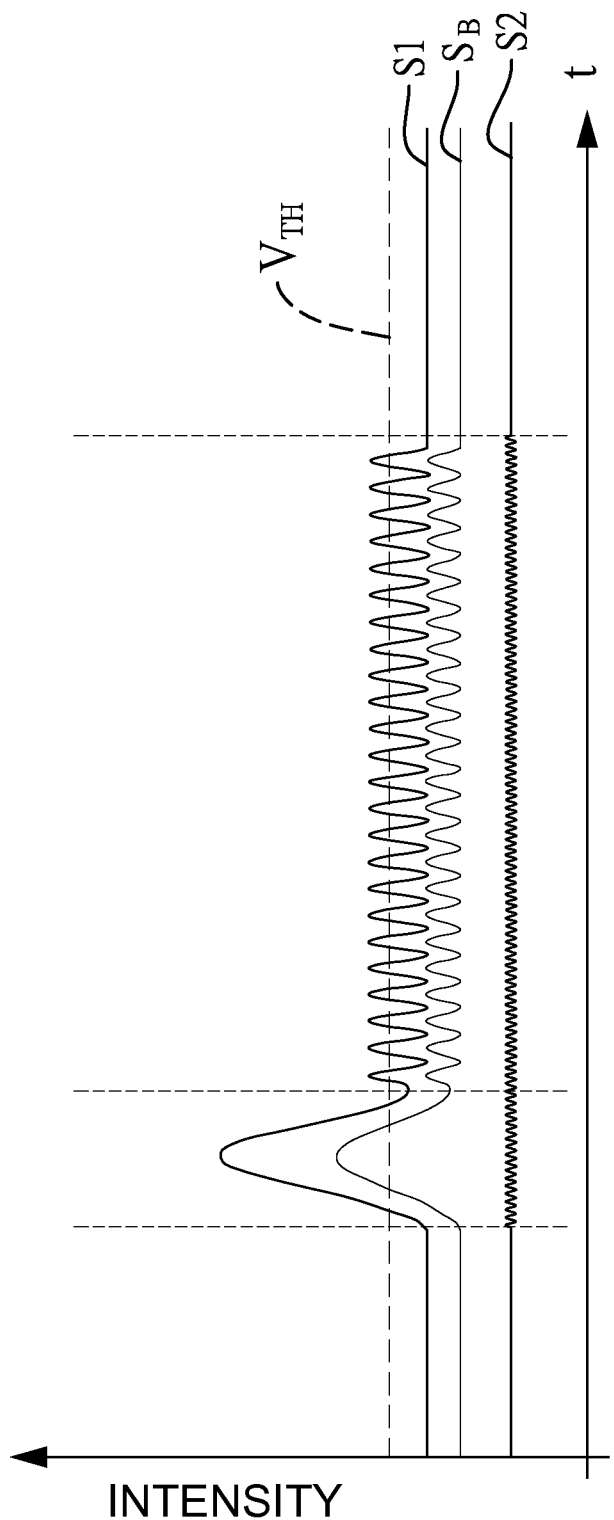
FIG. 4 is a waveform diagram of a base signal, a first signal and a second signal.

In the lower-scaled-signal mode, the processor 13 controls the brightness-sensing unit 11 to generate a second signal S2, such that the processor 13 can receive the second signal S2 from the brightness-sensing unit 11 (STEP 108). With reference to FIG. 1, in this embodiment, the processor 13 transmits a second control command C2 to the gain controller 113. Based on the second control command C2, the gain controller 113 activates the signal amplifier 112 to scale the intensity of the base signal $S_B$ by N time(s), wherein N is a positive number and N<M. For example, with reference to FIG. 4, when N is smaller than 1, the base signal $S_B$ is scaled down to form the second signal S2. As illustrated in FIG. 4, the second signal S2 is much weaker than the first signal S1.

When the processor 13 receives the second signal S2, the processor 13 determines whether the intensity of the second signal S2 is higher than the threshold value $V_{TH}$ (STEP 109). When the intensity of the second signal S2 is lower than the threshold value $V_{TH}$, the processor 13 controls the optical shutter 12 to operate in the bright state, such that the user can see the work piece during the grinding process via the optical shutter (STEP 110).

When the user performs the welding fabrication process again and a new welding arc is struck, the intensity of the second signal S2 would be rapidly increased to be higher than the threshold value $V_{TH}$. Hence, in STEP 109, when the processor 13 determines the second signal S2 is higher than the threshold value $V_{TH}$, the processor 13 automatically returns to STEP 102 to perform the higher-scaled-signal mode. In the higher-scaled-signal mode, as mentioned above, the optical shutter 12 can protect the user's eyes from welding arc.

What is claimed is:

1. An auto-darkening filter of a welding shield, the auto-darkening filter comprising:
   a brightness-sensing unit generating a first signal or a second signal, the first signal obtained from a base signal scaled by M time(s), the second signal obtained from the base signal scaled by N time(s), and N<M;
   wherein the brightness-sensing unit comprises
      an optical sensor generating the base signal directly proportional to environmental brightness sensed by the optical sensor;
      a signal amplifier connected to the optical sensor; and
      a gain controller connected to the signal amplifier;
   an optical shutter operating in a bright state or a dark state; and
   a processor connected to the signal amplifier, the gain controller, and the optical shutter, wherein
      the processor sends a control command to the gain controller, and the gain controller activates the signal amplifier to generate the first signal or the second signal according to the control command;
      when the processor operates in a higher-scaled-signal mode, the processor controls the brightness-sensing unit to generate the first signal, controls the optical shutter to operate in the dark state during a period that the first signal is higher than a threshold value, and controls the optical shutter to operate in the bright state during a period that the first signal is lower than the threshold value; and the processor changes to a lower-scaled-signal mode from the higher-scaled-signal mode when a change-mode command is received; in the lower-scaled-signal mode, the processor controls the brightness-sensing unit to generate the second signal, controls the optical shutter to operate in the bright state during a period that the second signal is lower than the threshold value, and changes to the higher-scaled-signal mode from the lower-scaled-signal mode when the second signal is higher than the threshold value and remains in the higher-scaled-signal mode after the first signal is no longer higher than the threshold value until the change-mode command is received.

2. The auto-darkening filter as claimed in claim 1, wherein the optical shutter is a liquid crystal shutter.

3. The auto-darkening filter as claimed in claim 2, wherein the optical shutter has better lightproof capability operating in the dark state than operating in the bright state.

4. The auto-darkening filter as claimed in claim 1, wherein the optical shutter has better lightproof capability operating in the dark state than operating in the bright state.

* * * * *